(12) United States Patent
Wu et al.

(10) Patent No.: US 8,815,107 B2
(45) Date of Patent: Aug. 26, 2014

(54) METHOD OF ETCHING SURFACE LAYER PORTION OF SILICON WAFER AND METHOD OF ANALYZING METAL CONTAMINATION OF SILICON WAFER

(75) Inventors: Jiahong Wu, Saga (JP); Shabani B. Mohammad, Saga (JP)

(73) Assignee: Sumco Corporation, Tokyo (JP)

( * ) Notice: Subject to any disclaimer, the term of this patent is extended or adjusted under 35 U.S.C. 154(b) by 84 days.

(21) Appl. No.: 13/238,652

(22) Filed: Sep. 21, 2011

(65) Prior Publication Data

US 2012/0077290 A1    Mar. 29, 2012

(30) Foreign Application Priority Data

Sep. 27, 2010    (JP) ................. 2010-215058

(51) Int. Cl.
*H01L 21/306*    (2006.01)
*H01L 21/66*    (2006.01)
*G01N 1/32*    (2006.01)

(52) U.S. Cl.
CPC .......... *H01L 21/30604* (2013.01); *H01L 22/12* (2013.01); *G01N 1/32* (2013.01)
USPC .................. 216/79; 438/706; 216/58; 216/59

(58) Field of Classification Search
CPC ................... H01L 21/32135; H01L 21/02019; H01L 22/12; H01L 21/30604; G01N 1/32
USPC ................... 408/706; 216/58, 59, 79
See application file for complete search history.

(56) References Cited

U.S. PATENT DOCUMENTS

| | | | | |
|---|---|---|---|---|
| 4,971,654 A | * | 11/1990 | Schnegg et al. | 438/752 |
| 5,916,824 A | * | 6/1999 | Mayuzumi et al. | 438/753 |
| 6,077,451 A | * | 6/2000 | Takenaka et al. | 216/79 |
| 7,686,973 B2 | | 3/2010 | Hirano et al. | |
| 2002/0101576 A1 | * | 8/2002 | Shabani et al. | 356/36 |
| 2004/0232111 A1 | | 11/2004 | Hirano et al. | |
| 2008/0047934 A1 | * | 2/2008 | Hirano et al. | 216/99 |
| 2008/0138996 A1 | * | 6/2008 | Nishizuka | 438/726 |

FOREIGN PATENT DOCUMENTS

| | | |
|---|---|---|
| JP | 3473699 | 9/2003 |
| JP | 3933090 | 3/2007 |

* cited by examiner

*Primary Examiner* — Fernando L Toledo
*Assistant Examiner* — Peter Bradford
(74) *Attorney, Agent, or Firm* — Greenblum & Bernstein, P.L.C.

(57) ABSTRACT

An aspect of the present invention relates to a method of etching a surface layer portion of a silicon wafer comprising: positioning the silicon wafer within a sealed vessel containing a mixed acid A of hydrofluoric acid and sulfuric acid so that the silicon wafer is not in contact with mixed acid A; introducing a solution B in the form of nitric acid containing nitrogen oxides into the sealed vessel and causing solution B to mix with mixed acid A; and vapor phase decomposing the surface layer portion of the silicon wafer within the sealed vessel within which mixed acid A and solution B have been mixed.

5 Claims, 5 Drawing Sheets

METHOD OF ETCHING SURFACE LAYER PORTION OF SILICON WAFER AND METHOD OF ANALYZING METAL CONTAMINATION OF SILICON WAFER

CROSS-REFERENCE TO RELATED APPLICATIONS

This application claims the benefit of priority under 35 USC 119 to Japanese Patent Application No. 2010-215058, filed on Sep. 27, 2010, which is expressly incorporated herein by reference in its entirety.

BACKGROUND OF THE INVENTION

1. Field of the Invention

The present invention relates to a method of etching a surface layer portion of a silicon wafer, more particularly, to a method of etching a surface layer portion of a silicon wafer that is suitable as a method of etching a surface layer portion of a silicon wafer to analyze metal contamination of the silicon wafer. Still more particularly, the present invention relates to an etching method that is capable of etching a surface layer portion of a silicon wafer in the direction of depth thereof with in-plane uniformity.

The present invention further relates to a method of analyzing metal contamination of a silicon wafer employing the above etching method.

2. Discussion of the Background

As semiconductor devices have become smaller and more highly integrated in the field of semiconductor manufacturing, trace metal impurities on the surface of the semiconductor substrate have been reported to affect device characteristics by producing leak defects and gate oxide integrity defects, shortening service lifetime, and the like. Further, not just contamination by metal impurities on the surface of the semiconductor substrate, but trace metal impurity contamination in areas of the surface layer of a semiconductor wafer on which device structures such as shallow trenches, sources, and drains are formed are also viewed as problems that affect device characteristics.

Conventionally, quantitative analysis methods in which the surface layer portion of a silicon wafer is dissolved in an acid solution, the acid solution is diluted or concentrated, and then the diluted or concentrated solution is subjected to quantitative analysis by atomic absorption spectrometry (AAS) or inductively coupled plasma mass spectrometry (ICP-MS) (referred to as "liquid phase etching methods" hereinafter), have been employed as methods of evaluating metal impurities on the surface and surface layer portions of silicon wafers. However, when employing the liquid phase etching method, uniform etching of the surface layer of a silicon wafer requires a large quantity of acid solution. Accordingly, inadequate sensitivity results from dilution of the metal impurity concentration by the large quantity of acid solution employed. Further, decreased sensitivity results from a heightened analysis background because of the introduction of contaminants from the acid solution itself. Both of these hinder highly sensitive analysis in the field of semiconductor manufacturing field, in which the evaluation of extremely small quantities of metal impurities is required.

Accordingly, methods in which the surface layer portion of a silicon wafer is decomposed with an acid vapor (etching gas), the decomposition residue is collected, and then the collected residue is subjected to quantitative analysis by AAS or ICP-MS (referred to as "vapor phase etching methods" hereinafter) have been proposed in recent years as substitute methods for the liquid phase etching methods. Such methods are proposed in Document 1 (Japanese Patent No. 3,473,699) as well as English language family members US2008/047934 A1, U.S. Pat. No. 7,686,973, and US2004/232111 A1, and Document 2 (Japanese Patent No. 3933090), which are expressly incorporated herein by reference in their entirety.

The vapor phase etching method described in Document 1 affords advantages in that only a small quantity of acid solution is needed for etching and the quantity of contamination introduced by the acid solution itself is much smaller than in liquid phase etching. However, in vapor phase etching methods in general, the acid (acid vapor) and semiconductor substrate react slowly. Accordingly, there is a problem in the form of low analysis sensitivity due to the low depth of etching per unit time. Although it is possible to increase the depth of etching by conducting the etching reaction for an extended period, analysis requiring long periods is undesirable from the perspective of enhancing productivity.

By contrast, in the vapor phase etching method described in Document 2, the surface of the silicon wafer is etched with a vapor produced from a mixed acid comprising hydrofluoric acid, nitric acid, and sulfuric acid (and optionally containing pieces of silicon). Nitric monoxide, NO, that is produced by the reaction serves as a catalyst, thereby shortening the etching time.

However, it is difficult to control the quantity of gas that is generated in conventional vapor phase etching methods, including the method described in Document 2. Thus, the amount of etching of the wafer tends to be nonuniform within the surface. This results in reduced analysis precision in the course of depth profile analysis of metal impurity distribution. It also becomes difficult to accurately compare metal contamination of the surface layer portions between wafers. Still further, when selectively analyzing just the epitaxial layer present on the extreme outer layer portion of a wafer, some portions within the surface end up being etched all the way to the underlayer of the epitaxial layer when the etching amount of wafer is nonuniform within the surface, resulting in a substantial drop in analysis precision.

SUMMARY OF THE INVENTION

An aspect of the present invention provides for means for rapidly and uniformly etching the surface layer portion of a silicon wafer by a vapor phase etching method.

The present inventors conducted extensive research into achieving the above means. As a result, they discovered that by generating a gas from a mixed acid of hydrofluoric acid and sulfuric acid in a sealed vessel in which a silicon wafer had been positioned, and then introducing nitric acid containing nitrogen oxides (NOx) into the sealed vessel, the wafer could be uniformly and rapidly etched with in-plane uniformity. The reasons for this were presumed by the present inventors to be as follows.

When a mixed acid of hydrofluoric acid and sulfuric acid is placed within a sealed vessel prior to vapor phase etching, hydrogen fluoride gas (HF) produced by the mixed acid can fill the space above the silicon wafer within the vessel. When nitric acid containing NOx (nitrogen oxides such as NO and $NO_2$) is added, the NOx in the nitric acid can catalyze the silicon wafer etching reaction due to the HF and the $HNO_3$ that are produced within the sealed vessel ($3Si(s)+18HF(g)+4HNO_3(g) \rightarrow 3SiF_6H_2(s)+4NO(s)+8H_2O(g)$). That is thought to accelerate the reaction rate (etching rate). In addition to the above, it is presumed that, by uniformly filling the space above the silicon wafer with HF prior to the above etching reaction, etching rate and in-plane uniformity of etching can be enhanced. Furthermore, the fact that NOx gas (NO) is uniformly generated from the surface of the wafer by the etching reaction is also presumed to contribute to the in-plane uniformity of etching.

The present invention was devised based on the above knowledge.

An aspect relates to a method of etching a surface layer portion of a silicon wafer comprising:

positioning the silicon wafer within a sealed vessel containing a mixed acid A of hydrofluoric acid and sulfuric acid so that the silicon wafer is not in contact with mixed acid A;

introducing a solution B in the form of nitric acid containing nitrogen oxides into the sealed vessel and causing solution B to mix with mixed acid A; and vapor phase decomposing the surface layer portion of the silicon wafer within the sealed vessel within which mixed acid A and solution B have been mixed.

The above etching method may further comprise preparing solution B by adding a piece of silicon in a mixed acid of nitric acid and hydrofluoric acid.

The sealed vessel may be of a cylindrical shape.

A further aspect of the present invention relates to a method of analyzing metal contamination of a silicon wafer comprising:

etching a surface layer portion of the silicon wafer by the above etching method;

collecting metal components on a surface of the silicon wafer following the etching in a collection liquid; and analyzing the metal components in the collection liquid.

The above analyzing method may further comprise evaluating process contamination based on a result of the analyzing.

The present invention permits the rapid etching of the surface layer portion of a silicon wafer in the direction of depth thereof with in-plane uniformity. It thus becomes possible to rapidly evaluate with high precision the metal contamination in the surface layer portion of the silicon wafer that negatively affects device characteristics.

Other exemplary embodiments and advantages of the present invention may be ascertained by reviewing the present disclosure and the accompanying drawings.

BRIEF DESCRIPTION OF THE DRAWINGS

The present invention will be described in the following text by the exemplary, non-limiting embodiments shown in the figure, wherein.

DETAILED DESCRIPTION OF THE EMBODIMENTS

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description taken with the drawings making apparent to those skilled in the art how several forms of the present invention may be embodied in practice.

An aspect of the present invention relates to a method of etching a surface layer portion of a silicon wafer by vapor phase decomposition, that is, to a method of etching by contacting the surface of a silicon wafer with a gas. The etching method of the present invention comprises: positioning the silicon wafer within a sealed vessel containing a mixed acid A of hydrofluoric acid and sulfuric acid so that the silicon wafer is not in contact with mixed acid A; introducing a solution B in the form of nitric acid containing nitrogen oxides into the sealed vessel and causing solution B to mix with mixed acid A; and vapor phase decomposing the surface layer portion of the silicon wafer within the sealed vessel within which mixed acid A and solution B have been mixed. As set forth above, this permits rapid etching with in-plane uniformity in the direction of depth of the surface layer portion of the silicon wafer.

The etching method of the present invention will be described in greater detail below.

Figure 1:
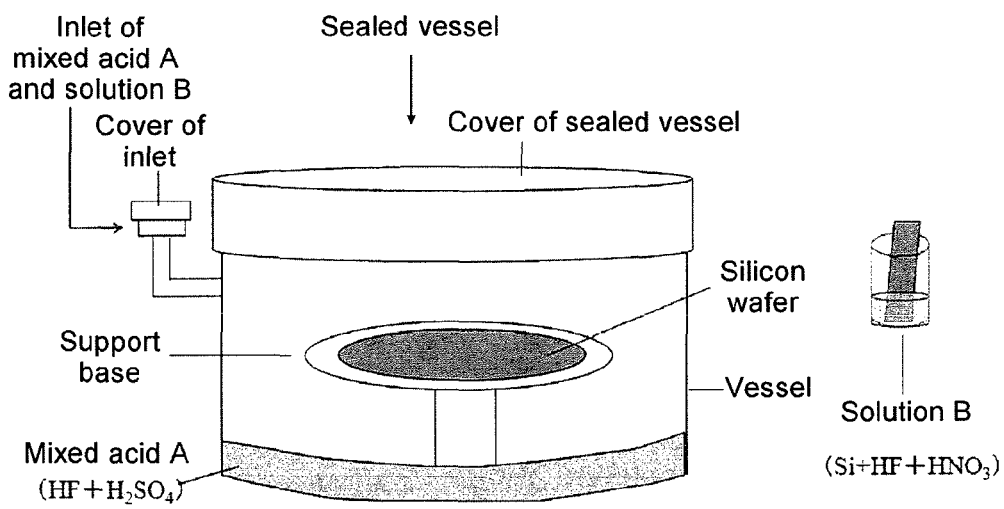
FIG. 1 is a schematic of the etching method of the present invention.

FIG. 1 is a schematic of the etching method of the present invention.

A sealed vessel configured such that a vessel in which a silicon wafer has been positioned can be sealed with a cover in the manner shown in FIG. 1, for example, can be employed in the present invention. It is desirable for the sealed vessel to be of a cylindrical shape such as that shown in FIG. 1 so that the etching gas spreads uniformly over the wafer surface. When an angular shape—such as a shape with a square plan view—is employed, the etching gas sometimes collects in the corners, tending not to uniformly spread over the surface of the wafer.

The silicon wafer that is to be etched is positioned within the sealed vessel so as not to be in contact with mixed acid A. To this end, for example, the silicon wafer is positioned on a support base provided in the sealed vessel as shown in FIG. 1 with the surface that is to be etched facing upward, mixed acid A is introduced through an inlet provided in the lateral surface of the vessel as shown in FIG. 1, and the cover of the inlet through which mixed acid A has been introduced is closed to seal the vessel. The support base and sealed vessel employed are desirably made of a highly acid-resistant plastic that does not dissolve and is not denatured by the acids that are introduced into the vessel. For example, the support base can be made of polytetrafluoroethylene (PTFE) and the sealed vessel of polyvinyl chloride.

Hydrofluoric acid (HF) with a concentration of 40 to 50 weight percent and sulfuric acid ($H_2SO_4$) with a concentration of 50 to 98 percent, for example, can be employed to prepare mixed acid A. To ensure that HF is quickly produced and rapidly and uniformly diffuses throughout the space above the silicon wafer in the vessel after the hydrofluoric acid and sulfuric acid have been mixed, the mixing ratio of hydrofluoric acid and sulfuric acid is desirably hydrofluoric acid:sulfuric acid (by volume)=3 to 6:1 to 3. For example, when a silicon wafer 200 mm in diameter is positioned on a support base about 5 to 10 cm in height, it is suitable to employ a cylindrical sealed vessel that is about 30 cm in diameter and about 15 cm in height. In that case, a mixed acid of 400 to 600 g of hydrofluoric acid (for example, EL grade 50 percent) and 100 to 300 g of sulfuric acid (for example, EL grade 98 percent) is desirably placed within the sealed vessel. To disperse with adequate uniformity the HF that is produced in the space above the silicon wafer, solution B is desirably not introduced into the vessel for about 3 to 5 minutes after positioning the silicon wafer.

In the present invention, nitric acid containing NOx (solution B) is prepared separately from the above operations. Examples of methods of preparing solution B are: (1) the method of preparing solution B by immersing a piece of silicon in a mixed acid of nitric acid and hydrofluoric acid; and (2) the method of diluting fuming nitric acid. In method (1), NOx is produced by reacting nitric acid, hydrofluoric acid, and Si as set forth above to obtain nitric acid containing NOx (solution B). For example, solution B can be prepared with nitric acid with a concentration of 50 to 70 weight percent. The hydrofluoric acid used to prepare solution B is as described for mixed acid A above. The Si employed to prepare solution B is not specifically limited. For example, pieces of silicon obtained by cutting a product wafer can be employed. From the perspective of getting the reaction that produces NOx and the vapor phase decomposition reaction following mixing with mixed acid A to proceed smoothly, the mixing ratio of nitric acid and hydrofluoric acid is desirably nitric acid:hydrofluoric acid (by volume)=16 to 24:2 to 5.

Pieces of silicon wafer obtained by cutting a silicon wafer product as set forth above are an example of the pieces of silicon that are immersed in the mixed acid in method (1). Specifically, solution B can be prepared by immersing pieces of silicon (for example, length×width×thickness=10×5×0.07 cm) for 2 to 5 minutes in a mixed acid obtained by mixing 100 mL of nitric acid (for example, EL grade 68 percent) and 20 mL of hydrofluoric acid (EL grade 50 percent), and then removing the silicon pieces. Immersion for 2 to 5 minutes in the mixed acid causes the silicon pieces to react with the hydrofluoric acid and nitric acid, producing NOx. In this process, 0.3 to 1.0 g of silicon normally dissolves.

In method (2), nitric acid containing NOx (solution B) can be obtained by diluting fuming nitric acid to 50 to 70 percent (by volume).

The solution B that is prepared is introduced into the sealed vessel containing mixed acid A and the silicon-wafer. For example, in the same manner as mixed acid A, solution B is introduced through an inlet provided in the lateral surface of the vessel as shown in FIG. 1, and the cover is applied over the inlet to seal the vessel. Subsequently, the sealed vessel is desirably rapidly shaken (rotated) several times (for example, two to three times) in such a manner that the solution does not get on the silicon wafer to uniformly mix mixed acid A and solution B.

Within the sealed vessel in which mixed acid A and solution B have been mixed as set forth above, the HF and $HNO_3$ that are produced by the mixed solution of mixed acid A and solution B come into contact with the surface of the silicon wafer, inducing vapor phase decomposition. At the start of the reaction, the NOx contained in solution B vaporizes to exhibit a catalytic effect. As the reaction progresses, NOx generated from the surface of the silicon wafer along with the etching reaction plays a catalytic role, causing the etching reaction to progress rapidly. By uniformly filling the space above the silicon wafer with HF before conducting the etching reaction and by uniformly generating NOx from the surface of the silicon wafer as the etching reaction progresses, it is possible to increase the in-plane uniformity of the depth of etching. As set forth above, it is desirable to rapidly shake the sealed vessel in such a manner that the solution does not get on the silicon wafer after introducing mixing solution B and mixing it with mixed acid A in the sealed vessel. This makes it possible to render the atmosphere within the sealed vessel uniform. However, the uniform generation of NOx from the wafer surface while the etching reaction is in progress is thought to contribute to uniformity in the depth of etching as set forth above. Thus, it is desirable to conduct the vapor phase decomposition with the sealed vessel in a stable state so that the uniformly generated NOx is not dispersed from the space over the silicon wafer. The depth of etching can generally be determined based on the depth of the surface layer region to be analyzed for metal contamination. In the analysis of ordinary metal contamination of the surface layer portion, the region to be analyzed in the direction of depth of the wafer surface is about 0.02 to 10 µm. It suffices to determine the period of vapor phase decomposition based on the desired depth of etching. It is not necessary to control the temperature or pressure in the above step. At room temperature under atmospheric pressure, the etching reaction will proceed adequately. The mixing ratio of solution B and mixed acid A is suitably former:latter=about 1:5 (by volume).

The etching method of the present invention as set forth above makes it possible to etch the surface layer portion of a silicon wafer by the decomposition sublimation of Si on the surface layer portion of the silicon wafer. In the course of analyzing the distribution of metal contamination in the direction of depth from the surface of the silicon wafer (depth-profile analysis), etching can be conducted in multiple cycles. To that end, it suffices to temporarily open the cover of the sealed vessel and discharge the gas from the vessel once etching has ended, and then conduct etching again by the method of the present invention.

The metal impurities that are contained in the surface layer portion that has been etched remain on the surface of the silicon wafer following vapor phase decomposition (the metal impurity layer that remains is also referred to as the "etching layer" hereinafter). Accordingly, the metal components can be recovered from the silicon wafer surface following etching and their quantities measured to obtain the level of metal contamination of the surface layer portion as concentrations of metal impurities contained in the surface layer portion that has been etched.

The metal components in the etching layer can be collected in a collection liquid by scanning the surface of the silicon wafer with a collection liquid. The collection liquid that is employed can be a mixed solution of pure water, hydrofluoric acid, and hydrogen peroxide solution; a mixed solution of pure water, hydrogen peroxide, and hydrochloric acid; a mixed solution of pure water, hydrofluoric acid, hydrogen peroxide solution, and hydrochloric acid; or the like. Reference can be made to Japanese Unexamined Patent Publication (KOKAI) No. 2005-265718, which is expressly incorporated herein by reference in its entirety or the like for collection liquids that can be employed. The quantity of collection liquid that is fed onto and scanned the silicon wafer surface is suitably about 50 to 250 µl.

For example, the method of tilting and rotating the wafer so that a liquid applied dropwise to the silicon wafer surface wets the entire surface can be employed to scan the collection liquid over the entire silicon wafer surface. This method can be conducted either manually or automatically.

Next, the metal components in the collection liquid that has been scanned over the surface of the silicon wafer can be analyzed to qualitatively and quantitatively analyze the metal components contained in the surface layer portion of the substrate that has been removed by etching. The metal components can be analyzed by a known method that permits the analysis of metal components in solution. Examples of such methods are atomic absorption spectrometry (AAS) and inductively coupled plasma mass spectrometry (ICP-MS). AAS and ICP-MS are desirable because they permit the high precision analysis of trace metal components. Examples of metals that can be analyzed are metals such as Ag, Cu, Li, Na, Mg, Al, K, Ca, Cr, Fe, Ni, Zn, and Mo.

The metal components that are contained in the surface layer portion that has been etched and remain on the surface of the silicon wafer can also be collected and analyzed by the one drop sandwich etching—inductively coupled plasma mass spectrometry (DSE-ICP-MS) method. For example, the mixing ratio of hydrofluoric acid and nitric acid can be adjusted to within a range suitable for collection of the metal components by the DSE method. This mixing ratio is desirably set to within a range permitting collection of the metal components that remain on the surface without dissolving the silicon wafer. For example, when collecting metal components on a wafer 200 mm in diameter, it is desirable to employ a collection liquid obtained by mixing these acids in a ratio of hydrofluoric acid (concentration 38 weight percent):nitric acid (concentration 68 weight percent)=100 to 200 µl:1,600 to 1,700 µl. When contamination by trace quantities of silicon is a concern, the collection liquid that has been used to collect the metal components can be dripped onto, and heated on, a clean wafer that has been positioned on a hot plate to cause the silicon to sublime (thereby removing it). Subsequently, the metal components that remain on the clean wafer can be collected with, for example, the above-described mixed solution of hydrofluoric acid and hydrogen peroxide, and the metal contamination components can be analyzed by ICP-MS to qualitatively and quantitatively analyze the metal components contained in the surface layer portion that has been etched.

A further aspect of the present invention is a method of analyzing metal contamination of a silicon wafer, comprising: etching a surface layer portion of the silicon wafer by the etching method of the present invention; collecting metal components on a surface of the silicon wafer following the etching (etching layer) in a collection liquid; and analyzing the metal components in the collection liquid.

The method of analyzing metal contamination of the present invention can be employed as a method of evaluating wafers to determine process contamination, such as contamination of the epitaxial layer in an epitaxial processing step and contamination of the surface layer of the wafer in a manufacturing step such as a heat treatment process. The surface layer portion that is etched to analyze metal contamination refers to the region in the direction of depth from the surface of the silicon wafer. The regions that should be analyzed differ based on the use and required physical properties of the silicon wafer. Thus, the analysis region is desirably determined based on the objective. To evaluate metal contamination of the surface layer portion without the surface, it suffices to clean the surface to remove metal impurities on the surface and then etch and analyze the surface layer portion. The cleaning liquid that is employed can be a mixed solution comprising a hydrogen peroxide solution, hydrofluoric acid, and hydrochloric acid of about a 5 to 10 weight percent concentration.

The silicon wafer the surface layer portion of which is analyzed for metal contamination by the present invention can be a p-type or n-type semiconductor substrate. The thickness, although not specifically limited, is 600 to 1,000 pm by way of example. The analyzing method of the present invention can be applied to wafers with diameters of 200 mm, 300 mm, 450 mm, or any other size.

EXAMPLES

The present invention will be described in detail below based on examples. However, the present invention is not limited to the examples. The "percent" given in Examples is weight percent.

Example 1

To the vessel shown in FIG. 1 (30 cm in diameter×15 cm in height, made of polyvinyl chloride) was charged a mixed acid comprising 500 g of hydrofluoric acid (EL grade 50 percent) and 200 g of sulfuric acid (EL grade 98 percent). A silicon wafer 200 mm in diameter with top and bottom surfaces that had been processed to mirror finishes was then positioned on a support base made of PTFE, and the cover was installed to seal the vessel. The vessel was left standing for five minutes to allow the mixed acid to generate HF.

Separately from the above operation, a 0.3 g piece of silicon (L×W×H: 10 cm×5 cm×0.07 cm) was dissolved by immersion for two minutes in a mixed acid comprising 90 g of nitric acid (EL grade 68 percent) and 10 g of hydrofluoric acid (EL grade 50 percent) in a 250 mL beaker (8 cm in diameter).

Next, the solution in the beaker was introduced into the sealed vessel through a tube via an inlet provided in the lateral surface of the vessel. Subsequently, the lateral surface of the vessel was gripped by hand and the vessel was manually shaken side to side two or three times. The vapor phase decomposition reaction was then allowed to proceed with the vessel in a stable state from that point on.

Figure 2:
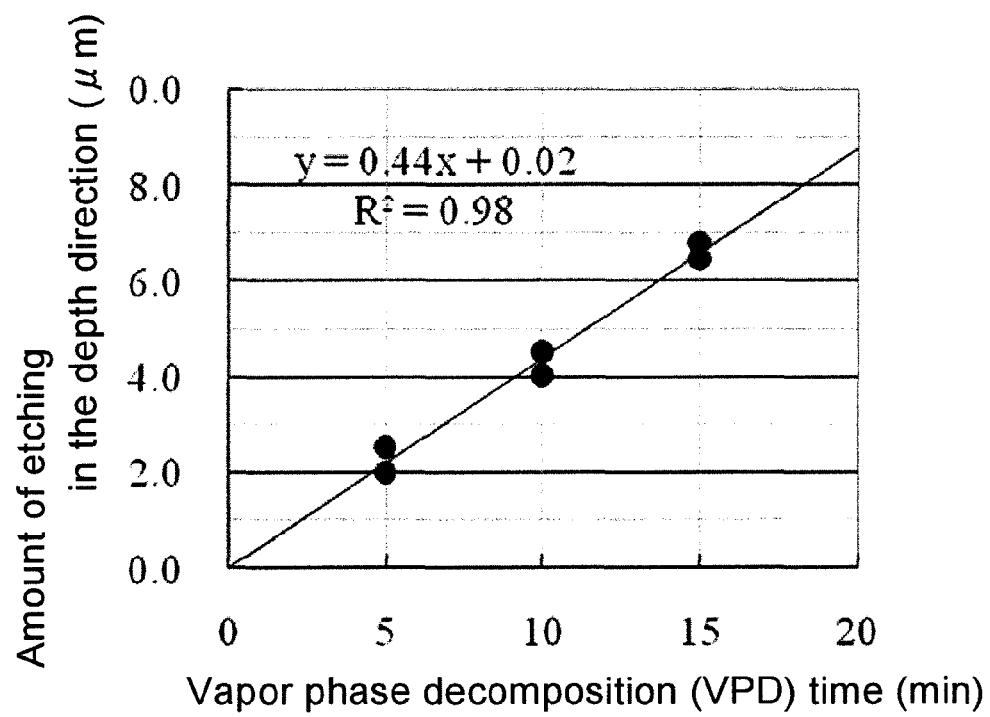
FIG. 2 shows the relation between the vapor phase decomposition time and depth of etching in Example 1.

The above steps were conducted at room temperature under atmospheric pressure without temperature or pressure regulation. Etching was conducted for a variety of standing times (vapor phase decomposition (VPD) time) to obtain multiple silicon wafers. The thickness of the center portion of each wafer was measured before and after etching, and the depth of etching was determined as the difference in thickness before and after etching. The results are given in FIG. 2. As will be seen from the results in FIG. 2, it was determined that etching to a depth of up to 7 μm could be conducted at an etching rate of about 0.45 gm/minute in the present Example.

To determine the in-plane uniformity of etching, the thickness of a silicon wafer that had been etched while being stable for a period of 15 minutes was measured in a linear direction running through the center of the wafer. The results are given in FIG. 3. As will be understood from FIG. 3, the in-plane uniformity of etching in the direction of depth was ±1 μm.

Comparative Example 1

Figure 4:
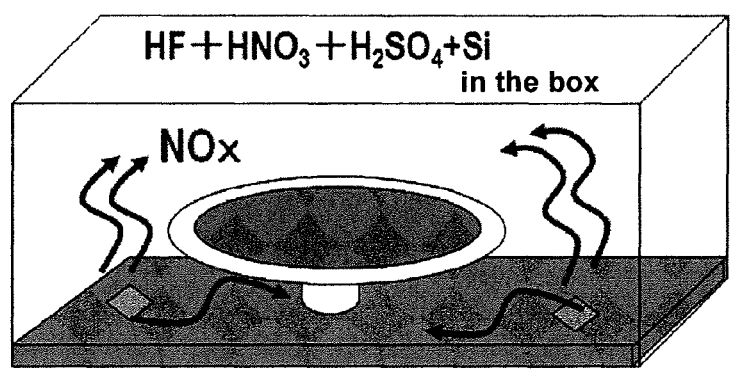
FIG. 4 is a schematic of the etching method of Comparative Example 1.

A mixed acid comprising 400 g of sulfuric acid (EL grade 98 percent), 180 g of nitric acid (EL grade 68 percent), and 1,000 g of hydrofluoric acid (EL grade 50 percent) containing a 1 g piece of silicon was placed in a sealed square vessel (L×W×H=45 cm×30 cm×15 cm) and silicon wafers identical to those in Example 1 were subjected to VPD for 15 minutes. FIG. 4 shows a schematic of the etching process in Comparative Example 1.

Subsequently, the thickness in a linear direction running through the center of the wafers was measured in the same manner as in Example 1. The results are given in FIG. 5. As will be understood from FIG. 5, with a difference in the in-plane thickness of about 8 μm, the results indicated poor in-plane etching uniformity in the direction of depth.

Figure 3:
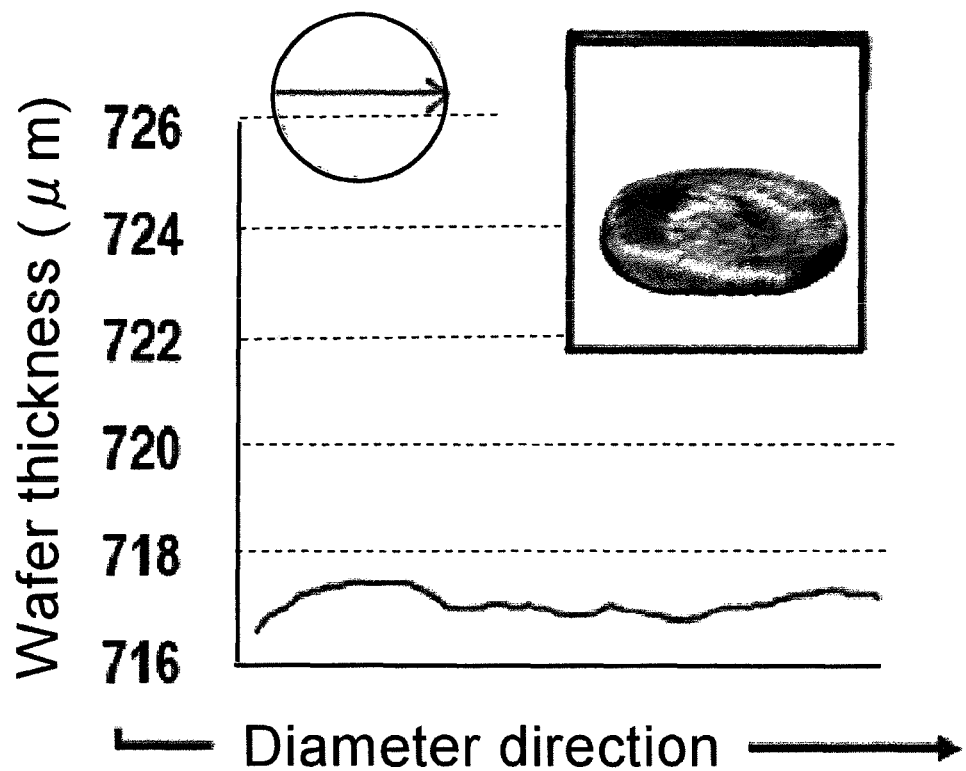
FIG. 3 shows the in-plane distribution of the depth of etching (in-plane uniformity of etching) on the surface of the silicon wafer that was vapor phase etched in Example 1.
Figure 5:
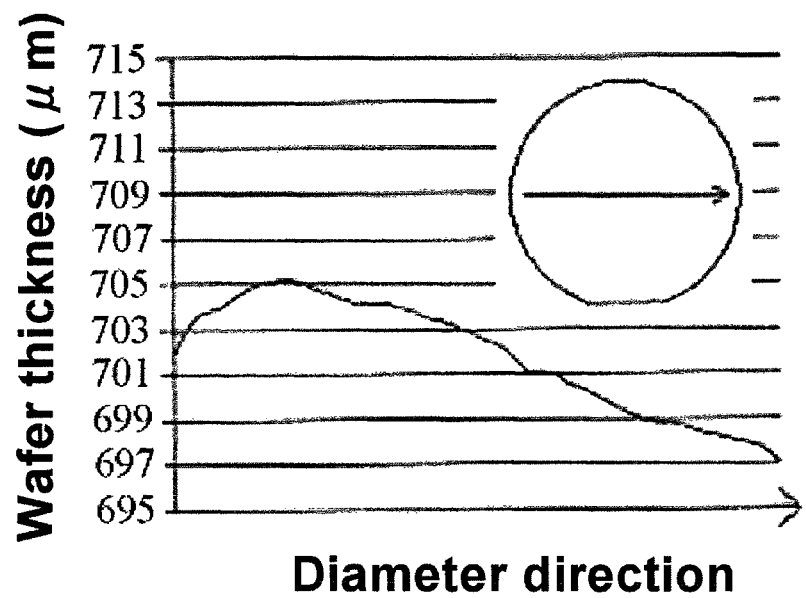
FIG. 5 shows the in-plane distribution of the depth of etching on the surface of the silicon wafer that was vapor phase etched in Comparative Example 1.
Figure 6:
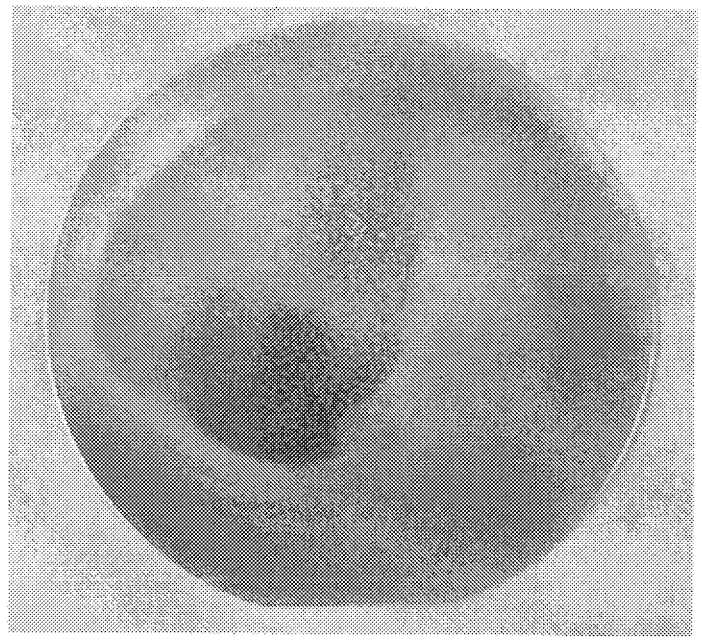
FIG. 6 is a digital camera photograph of the surface of the silicon wafer that was vapor phase etched in Comparative Example 1.

A comparison of FIGS. 3 and 5 reveals that in Example 1, etching was conducted with a more uniform amount of wafer in-plane etching than in Comparative Example 1. FIG. 6 shows a digital camera photograph of the surface of the wafer etched in Comparative Example 1. As shown in FIG. 6, nonuniformity in the glossiness of the surface etched in Comparative Example 1 also reveals that the depth of etching was nonuniform.

Example 2

A silicon wafer 200 mm in diameter with surfaces processed to mirror finishes that had been contaminated by spin coating with a quantity of Mo of about $1E+13$ atoms/cm$^2$ was annealed for 90 minutes at 950° C. in a nitrogen atmosphere and then cleaned with hydrofluoric acid. Subsequently, it was subjected to five cycles of vapor phase etching by the same method as in Example 1. With the completion of each cycle of vapor phase etching, the cover was removed from the sealed vessel, the silicon wafer was removed, 100 μl of an acidic collection liquid comprising 5 percent hydrofluoric acid/10 percent hydrochloric acid/5 percent hydrogen peroxide solution was applied dropwise to the surface of the etched wafer, the liquid was scanned over the entire surface of the wafer, and the metal impurities were collected. The collected solution was mixed with 1,000 μl of ultrapure water, and quantitative evaluation of Mo was conducted by high-sensitivity double-focusing ICP-MS.

Figure 7:
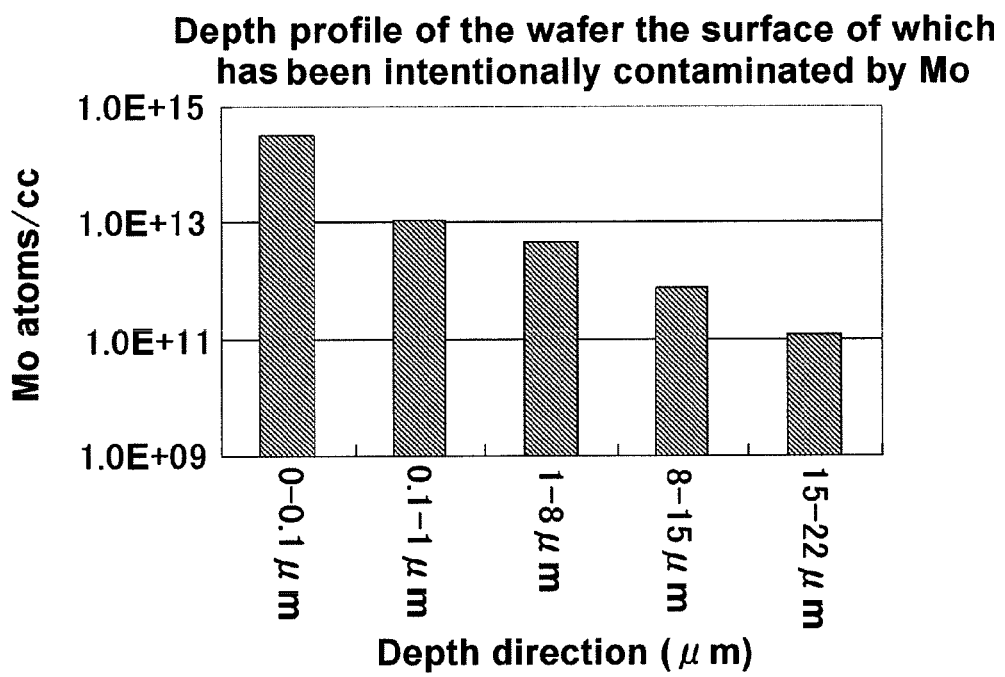
FIG. 7 shows results of analysis of the distribution of Mo contamination in the direction of depth obtained in Example 2.

FIG. 7 gives the results of distribution analysis (depth-profile analysis) of metal contamination in the direction of depth from the surface of the silicon wafer obtained by the above steps. The results shown in FIG. 7 indicate that the level of contamination varied in the direction of depth, with the level of contamination increasing with proximity to the wafer surface.

When the amount of in-plane etching was nonuniform in the manner of Comparative Example 1, certain in-depth portions ended up being etched more shallowly than the target region, and some regions ended up being etched more deeply than the target region. The metal contamination distribution analysis in the direction of depth that was conducted following such etching was of poor reliability. By contrast, the results given in FIG. 7 were obtained by uniform in-plane etching such as that shown in FIG. 3, and accurately show the Mo contamination distribution in the direction of depth. That is, the present invention makes it possible to analyze with high precision the metal contamination of the surface layer portion of a silicon wafer because it permits a uniform amount of in-plane etching of the wafer.

The present invention is useful in the field of semiconductor substrate manufacturing.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any Examples thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of etching a surface layer portion of a silicon wafer comprising:
    positioning the silicon wafer within a sealed vessel containing a mixed acid A of hydrofluoric acid and sulfuric acid so that the silicon wafer is not in contact with mixed acid A;
    introducing a solution B in the form of nitric acid containing nitrogen oxides into the sealed vessel and causing solution B to mix with mixed acid A; and
    vapor phase decomposing the surface layer portion of the silicon wafer within the sealed vessel within which mixed acid A and solution B have been mixed,
    wherein mixed acid A has a different chemical composition than solution B.

2. The method of etching according to claim 1, which further comprises preparing solution B by adding a piece of silicon in a mixed acid of nitric acid and hydrofluoric acid.

3. The method of etching according to claim 1, wherein the sealed vessel is of a cylindrical shape.

4. A method of analyzing metal contamination of a silicon wafer comprising:
    etching a surface layer portion of the silicon wafer by the method according to claim 1;
    collecting metal components on a surface of the silicon wafer following the etching in a collection liquid; and
    analyzing the metal components in the collection liquid.

5. The method of analyzing according to claim 4, which further comprises evaluating process contamination based on a result of the analyzing.

\* \* \* \* \*